United States Patent [19]

Burnett et al.

[11] Patent Number: 4,556,534

[45] Date of Patent: Dec. 3, 1985

[54] NICKEL BASED CASTING ALLOY

[75] Inventors: Arthur P. Burnett; Wayne C. Bollinger, both of York, Pa.

[73] Assignee: Dentsply Research & Development Corp., Milford, Del.

[21] Appl. No.: 563,556

[22] Filed: Dec. 20, 1983

[51] Int. Cl.$^4$ ............................................. C22C 19/05
[52] U.S. Cl. .................................. 420/445; 420/452; 433/207
[58] Field of Search ................ 420/442, 443, 445–454; 148/410, 427, 428; 433/207

[56] References Cited

U.S. PATENT DOCUMENTS

| | | |
|---|---|---|
| 1,942,150 | 1/1934 | Rohn . |
| 1,945,679 | 2/1934 | Corson . |
| 2,089,587 | 8/1937 | Toucada . |
| 2,621,122 | 12/1952 | Gresham et al. . |
| 2,631,095 | 3/1953 | Griffiths et al. . |
| 3,464,817 | 9/1969 | Griffiths . |
| 3,704,182 | 11/1972 | Griffiths et al. . |
| 3,749,570 | 7/1973 | Lyon . |
| 3,767,479 | 10/1973 | Tarshis . |
| 3,914,867 | 10/1975 | Manning et al. . |
| 4,038,752 | 8/1977 | Phelps et al. . |
| 4,049,427 | 9/1977 | Guerra . |
| 4,243,412 | 1/1981 | Tandon . |
| 4,288,247 | 9/1981 | Shaw . |
| 4,292,076 | 9/1981 | Gigliotti et al. . |

FOREIGN PATENT DOCUMENTS 1465157  2/1977  United Kingdom .
2038359  7/1980  United Kingdom .

OTHER PUBLICATIONS

American Dental Association Specification No. 5 for Dental Casting Gold Alloy, pp. 184–187—Specification for Dental Materials.
American National Standards Institute/American Dental Association Specification No. 14 for Dental Base Metal Casting Alloys—1982.
Dentsply/York Division—Cobond—Ceramic Bonding Alloy, pp. 1–6—Jul. 1982.
Dentsply/York Division—The Dentsply Biobond Technique, pp. 1–30—May 1982.
The Dentsply Technique to Biobond Acid Etched Resin Bonded Bridgework—Dentsply/York Division—Jan. 1983.
374—A Practical Test to Evaluate the Castability of Dental Alloys—R. P. Whitlock et al—p. 404.

*Primary Examiner*—R. Dean
*Attorney, Agent, or Firm*—Edward J. Hanson, Jr.

[57] ABSTRACT

A nickel base casting alloy containing 10 to 25 percent chromium, 3 to 8 percent manganese, 3 to 10 percent niobium, 0 to 3.5 percent aluminum, 0.5 to 2.0 percent beryllium which exhibits lower melting characteristics allowing enhanced compatibility to gypsum bonded investments.

14 Claims, No Drawings

NICKEL BASED CASTING ALLOY

RELATED APPLICATIONS

This application is related to copending application Ser. No. 521,485, filed Aug. 8, 1983.

BACKGROUND OF THE INVENTION

I. Field of Invention

This invention relates to low fusing nickel base alloys, particularly nickel base alloys which are useful for cast metallic structures for dental prosthetic devices or for cast jewelry. The alloys of the present invention are particularly useful for preparing cast structures in gypsum bonded investments.

Alloys of the general type with which the invention is concerned typically are characterized by their having resistance to corrosion in the oral environment, a tensile yield strength in excess of 40,000 psi, and good castability from temperatures lower than about 1,480° C. For compatibility with gypsum bonded investments, these alloys typically have a solidus temperature lower than about 1,150° C. and a liquidus temperature lower than about 1,260° C.

Preferred nickel base alloys of this type typically contain 10 to 20 percent chromium and 0 to 8 percent molybdenum with lesser amounts of tungsten, vanadium, tantalum, niobium, tin, aluminum, manganese, boron, iron, silicon, cobalt, carbon, or beryllium or combinations thereof.

II. Description of the Prior Art

The nickel-beryllium system as a binary eutectic is disclosed in depth in U.S. Pat. No. 3,704,182 to Griffiths. This patent also described the mechanism by which chromium participates in the eutectic reaction, and the use of columbium, also known as niobium and referred to hereinafter as niobium or Nb, as a hardening element in combination with solution heat treating at 1,090° to 1,175° C. followed by subsequent age hardening heat treatment.

The enhanced corrosion resistance in nickel-beryllium alloys with the addition of chromium in the 10 to 20 weight percent range is disclosed in U.S. Pat. No. 1,945,679 to Corson. This patent further discloses that the substitution of molybdenum and tungsten for chromium can be accomplished while maintaining corrosion resistance.

U.S. Pat. No. 2,089,587 to Touceda makes use of the excellent castability and corrosion resistance of nickel-chromium-beryllium alloy systems of the type disclosed in the above Corson and Griffiths patents, and discusses the use of systems of this type for casting dental prosthetic articles. Further refinement of alloys of this ternary system for applications in dental devices is discussed in U.S. Pat. No. 2,631,095 to Griffiths, which shows that additions of manganese to the system could give further control of the melting range of the alloys and that cobalt could be substituted for nickel over a wide range of compositions. In the compositions disclosed in U.S. Pat. No. 3,464,817 to Griffiths, the improvement in mechanical properties by the addition of aluminum was demonstrated.

The addition of aluminum to a nickel base alloy also is suggested by U.S. Pat. Nos. 2,621,122 to Gresham, 4,292,076 to Gigliotti, 3,464,817 to Griffiths, 3,749,570 to Lyon, and 4,049,427 to Guerra, and by United Kingdom Application GB No. 2038359 to Unitek.

The manganese effect is disclosed in U.S. Pat. No. 2,631,095 to Griffiths. The effect of manganese on the melting range of nickel-chromium-beryllium alloys is utilized in U.S. Pat. No. 3,464,817 to Griffiths to produce alloys castable in gypsum bonded investments.

Gypsum bonded investments are generally known to be desirable for lost wax casting of dental prosthetics and items of jewelry because they can provide excellent replication of surface detail. The utility of gypsum bonded investments is reduced or lost as the melting range of an alloy system is raised so that the casting temperature must increase; conversely, lowering the melting range of an alloy system improves the ability to utilize gypsum bonded investments.

OBJECTS AND SUMMARY OF THE INVENTION

A primary object of this invention is to provide nickel-chromium-beryllium base casting alloys with improved castability in gypsum bonded investments while maintaining the mechanical, physical, and corrosion resistance properties characteristic of alloys of the nickel-chromium-beryllium system.

Another object of this invention is to provide an alloy compatible with gypsum bonded investment suitable for use in the casting of jewelry, particularly for ring fabrication, wherein the alloy is characterized as having high ductility, good polishability, and excellent resistance to tarnish and corrosion.

It is still another object of the invention to provide a nickel-chromium-beryllium base casting alloy that exhibits superior dental porcelain bonding while maintaining its castability in gypsum bonded investments. Although no ANSI/ADA specification presently exists for porcelain fused to metal alloys, the alloys of this object may be characterized as exceeding the necessary mechanical requirements for dental prostheses—"Subjected to very high stress in thin cross section in the form of saddles, bars, clasps, thimbles, crowns, and unit castings" (ADA Specification Number 5, dated April 1965) while having a coefficient of thermal expansion of about $14 \times 10^{-6}$ in/in/°C.

Yet another object of this invention is to provide a nickel-chromium-beryllium base dental casting alloy having a microstructure that promotes selective etching to the extent that it provides retention to resin type materials while maintaining its excellent castability in gypsum bonded investments as well as its superior dental porcelain bonding characteristics.

Still another object of this invention is to provide a nickel-chromium-beryllium base alloy that is gypsum bonded investment compatible, and suitable for use as a cast "dental prosthetic device subjected to high stress; and cast into the form of thin ¾ crowns, thin cast backings, abutments, pontics, full crowns, and saddles" (ADA Specification Number 5, dated April 1965). Characteristically, this alloy will be low in hardness for nickel based alloys for minimizing wear when the alloy is used in opposition to natural dentition.

A further object of this invention is to provide a nickel-chromium-beryllium base, gypsum bonded investment compatible, dental casting alloy suitable for use as a framework for removable dentures. This alloy is characteristically to have the mechanical and corrosion resistance properties required of ANSI/ADA Specification Number 14, dated April 1982.

It is a still further object of the present invention to provide casting alloys, suitable for use in forming dental prostheses that are characterized by having microstructures that are selectively etchable to an extent that mechanical retention of resin type materials, such as denture bases, and veneering acrylics can be attached to the alloy surfaces.

These and other objects and advantages of the present invention are achieved by providing alloys based upon the nickel, chromium, manganese, niobium, beryllium alloy system, wherein the alloys are characterized by the niobium modification of the nickel-beryllium binary eutectic such as to lower substantially the solidus temperature from the 1,175° C. binary eutectic temperature to below about 1,090° C., for example, to about 1,050° to about 1,070° C. These alloys, which may be visualized as containing the broad and preferred compositional ranges set forth in Table 1, consist essentially of (by weight percent) 10 to 25 percent chromium, 3 to 10 percent niobium, 3 to 8 percent manganese, and 0.5 to 2 percent beryllium with the balance being nickel. Additionally, the alloys may contain up to about: 3.5 percent aluminum; 20 percent cobalt; 6 percent copper; 3 percent tin; 1 percent titanium; 5 percent vanadium; 8 percent (each or in combination) bolybdenum, tantalum, and tungsten; 1 percent (each or in combination) boron and carbon; 3 percent total rare earth elements including lanthanum, cerium, praseodymium, neodymium, and gadolinium; and incidental impurities; provided, however, that the alloys consist of at least about 71 percent by weight of nickel, chromium, niobium, manganese, and beryllium in combination.

TABLE 1

| Composition of Present Alloys (Percent by Weight) | | | |
|---|---|---|---|
| Broad Range | | Preferred Range | |
| Ni: | 52–84 | Ni: | 65–84 |
| Cr: | 10–25 | Cr: | 11–16 |
| (Cb)Nb: | 3–10 | (Cb)Nb: | 3.5–5.5 |
| Mn: | 3–8 | Mn: | 3.5–4.5 |
| Be: | 0.5–2.0 | Be: | 0.85–1.15 |
| Al: | 0–3.5 | Al: | 0.8–2.5 |
| Co: | 0–20 | Co: | 0–20 |
| Cu: | 0–6 | Cu: | 0–6 |
| Sn: | 0–3 | Sn: | 0–3 |
| Ti: | 0–1 | Ti: | 0–1 |
| V: | 0–5 | V: | 0–5 |
| Mo: Ta: W: | 0–8 | Mo: Ta: W: | 0–8 |
| B: C: | 0–1 | B: C: | 0–1 |
| Rare Earths: | 0–3 | Rare Earths: | 0–3 |

These alloys are producible by using generally accepted air melting foundry practices. It generally is preferred that the beryllium be added to the melt in the form of a nickel-beryllium or nickel-chromium-beryllium master alloy. The other elements may be added in master alloy or elemental form.

The alloys of the present invention exhibit an ultimate tensile strength of over about 80,000 psi, a 0.2 percent offset tensile strength of at least about 50,000 psi, and a coefficient of thermal expansion in the range of from about $13.0 \times 10^{-6}$ in/in/°C. to about $15.0 \times 10^{-6}$ in/in/°C.

DESCRIPTION OF THE INVENTION

Briefly stated, the alloys of this invention are based upon the nickel, chromium, manganese, niobium, beryllium alloy system and are characterized by the niobium modification of the nickel-beryllium binary eutectic such as to lower substantially the solidus temperature from the 1,175° C. binary eutectic temperature to about 1,050° C. to 1,070° C.

These alloys are producible by using generally accepted air melting foundry practices, and it is preferred that the beryllium be added to the melt in the form of a nickel-beryllium or nickel-chromium-beryllium master alloy. The other elements may be added in master alloy form or in elemental form.

The present invention, in its broader aspects, is an alloy castable in gypsum bonded investment and consisting essentially of about (by weight percent): 52 to 84 percent nickel, 10 to 25 percent chromium, 3 to 10 percent niobium, 3 to 8 percent manganese, and 0.5 to 2 percent beryllium. Additionally, the alloy may contain up to about: 3.5 percent aluminum; 20 percent cobalt; 6 percent copper; 3 percent tin; 1 percent titanium; 5 percent vanadium; 8 percent molybdenum, tantalum, and tungsten each or in combination; 1 percent boron and carbon each or in combination; 3 percent total rare earth elements including lanthanum, cerium, praseodymium, neodymium, and gadolinium; and incidental impurities; provided, however, that the alloy consists of at least about 71 percent by weight of nickel, chromium, niobium, manganese, and beryllium in combination.

In another somewhat narrower aspect of the invention, there is provided a series of dental casting alloys which exhibit properties suitable for veneering with dental porcelain. The preferred composition for alloys of this aspect of the invention is (by weight percent): 65 to 84 percent nickel, 11 to 16 percent chromium, 0.85 to 1.15 percent beryllium, 3.5 to 8 percent manganese, and 3 to 10 percent niobium. Alloys in accordance with this aspect of the invention optionally may contain up to 20 percent cobalt, up to 3 percent aluminum, up to 3 percent tin, up to 1 percent titanium, up to 5 percent vanadium, up to 8 percent molybdenum, tantalum, and tungsten each or in combination, up to 3 percent rare earth elements, and up to 1 percent boron and carbon each or in combination.

By another aspect of this invention, alloys particularly suited for casting removable partial denture frameworks are provided by an alloy consisting essentially of (by weight percent) 52 to 84 percent nickel, 10 to 25 percent chromium, 3 to 10 percent niobium, 3 to 8 percent manganese, 0.75 to 2 percent beryllium, 0.75 to 2.0 percent aluminum, and optionally up to 20 percent cobalt, up to 6 percent copper, up to 1 percent titanium, and up to 5 percent vanadium.

Still another aspect of this invention provides casting alloys that have mechanical properties particularly suitable for dental casting of single unit crowns, short span bridges, and splints that are further characterized by their having microstructures that can be electrochemically etched to produce undercuts in selectively attached surfaces that provide retention for resin type veneering materials. These alloys consist essentially of (by weight percent) 65 to 84 percent nickel, 10 to 20 percent chromium, 0.5 to 1.5 percent beryllium, 3 to 6 percent manganese, 3 to 8 percent niobium, and optionally up to 5 percent vanadium and up to 3 percent tin.

Still another aspect of this invention provides alloys with properties particularly suited for the casting of items of jewelry and these alloys consist essentially of (by weight percent) 65 to 84 percent nickel, 10 to 20 percent chromium, 0.75 to 2 percent beryllium, 3 to 8 percent manganese, 3 to 10 percent niobium, and optionally up to 5 percent vanadium, up to 3 percent tin, up to 10 percent cobalt, up to 1 percent titanium, and up to 2 percent aluminum.

The compositions of the present invention all employ nickel-chromium compositions for their generally recognized ability to give excellent corrosion resistance necessary for prolonged use in the environment of the human mouth.

The niobium functions in combination with the beryllium to substantially lower the alloy solidus temperature, while the manganese is believed to function in coordination with the beryllium to substantially lower the liquidus temperature. This combination significantly improves the melt fluidity and castability in gypsum bonded investments of the alloys of this invention over those of the prior art. The combination of chromium, niobium, manganese, and beryllium further serves to reduce the thermal expansion of the alloys from that of nickel to the range(s) desired for dental applications and more precisely for compatibility with dental porcelains.

The optional addition of small quantities of aluminum, while undesirably raising the thermal expansion, increases the tensile properties of the alloys considerably.

When the alloys of this invention are used as the substructure for dental porcelain, the oxidation characteristics of the alloys must be controlled through the alloy composition in combination with heat treatment, chemical surface treatment, and/or mechanical surface treatment to insure the alloy surface is chemically compatible with the porcelain to effect a stable bonding of the two materials. All the aforementioned elements potentially can influence the bonding mechanisms, apparently in both positive and negative ways, depending upon factors other than merely alloy composition though the mechanisms by which dental porcelains bond are not well understood.

The alloys of this invention generally are alloyable by ordinary air melting or vacuum melting techniques which are standard in foundry practice. During air melting, it may be desirable to employ an inert gas cover, also standard, to avoid loss of alloying constituents due to oxidation. In a preferred embodiment, the beryllium is added to the melt in the form of a nickel-beryllium or nickel-chromium-beryllium master alloy. Niobium may be added by using either a nickel-niobium master alloy or elemental niobium. Any other additions of alloying elements generally are made in order of increasing risk of loss due to oxidation or volatilization.

In a preferred production procedure, the alloys of this invention may be prepared by forming a melt of nickel, adding to the melt a nickel-chromium-beryllium master alloy, and then adding niobium, manganese, and aluminum. The resulting alloy then may be cast into ingots which will be remelted for the casting of dental metal substructures or prosthetic devices as well as items of jewelry. These castings are produced by conventional lost wax investment casting techniques routinely used in commercial dental laboratories and in the jewelry industry.

The following examples illustrate alloy compositions and their percentages by weight of the total composition when made in accordance with the principles of the invention as set forth herein:

EXAMPLES 1-3

A series of nickel base alloys with the compositions shown in Table 2 were prepared by induction melting in an alumina crucible under a cover of argon gas. The nickel charge was melted, then the beryllium addition was made from a master alloy of nickel containing 2.5 weight percent beryllium and 12 weight percent chromium. The balance of the chromium was added as elemental chromium. The niobium, manganese, and aluminum were then added. These alloys were poured at approximately 1,455° C. into graphite bar molds preheated to 150° C., then cut into approximately 5 gram ingots for remelting for casting of dental prostheses, items of jewelry and test samples for determining mechanical and physical properties.

The alloy ignots were remelted by gas-oxygen torch heating and induction melting equipment common to dental laboratory practice and cast into commercially available gypsum bonded investment molds.

TABLE 2

| Example | Alloy Constituents (Percent by Weight) | | | | | |
| --- | --- | --- | --- | --- | --- | --- |
| | Ni | Cr | Nb | Be | Mn | Al |
| 1 | Bal | 16.0 | 4.0 | 1.0 | 4.0 | — |
| 2 | Bal | 15.3 | 4.7 | 1.0 | 4.2 | 1.15 |
| 3 | Bal | 16.0 | 5.0 | 1.0 | 4.0 | 2.5 |

EXAMPLE 4

Mechanical Properties

The tensile properties of the alloys of Examples 1-3 (Table 2) in the as cast condition were determined by procedures detailed in ADA/ANSI Specification Number 14, dated April 1982. The hardness of the alloys was determined on metallographically finished samples in the as cast condition using a Tukon TM microhardness tester. The results of this testing, as shown in Table 3, demonstrate: the alloy of Example 1 exhibits the low hardness and high ductility desirable for alloys for single crowns as short span fixed dental prosthetic devices; the alloy of Example 2 exhibits the high yield strength and high ductility desirable for alloys for removable dental prosthetic devices; the alloys of Examples 1 and 2 exhibit the high ductility desirable for items of jewelry; and the alloys of Examples 2 and 3 exhibit the high yield strength desired in alloys for long span fixed dental prosthetic devices.

TABLE 3

| Mechanical and Physical Properties. | | | |
| --- | --- | --- | --- |
| | Alloy Example Number | | |
| | 1 | 2 | 3 |
| Ultimate Tensile Strength (psi) | 128,000 | 138,000 | 165,000 |
| 0.2 Percent Tensile Yield Strength (psi) | 78,000 | 105,000 | 146,000 |
| Elongation in one cm (%) | 32 | 23 | 10 |
| Hardness ($HV_{1\ kg}$) | 260 | 340 | 415 |
| Solidus Temperature °C. | 1,060 | 1,060 | 1,060 |
| Liquidus Temperature °C. | 1,230 | 1,230 | 1,230 |

EXAMPLE 5

Melting Range

The melting range of the alloys of Examples 1-3 was determined using a Stone TM differential thermal analyzer and was verified by scanning electron microscopy on test samples quenched from below, within, and above the temperature reported in Table 3. All the alloys of Examples 1-3 exhibit the reduction of solidus temperature from that of the nickel-beryllium eutectic temperature that contribute to the improved castability in gypsum bonded investments.

EXAMPLE 6

Dental Porcelain Compatibility

The thermal expansion of the alloy of Example 3 was determined to be $14 \times 10^{-6}$ in/in/°C. over the temperature range 25° to 500° C. using a Perkin Elmer TM Thermal-Mechanical Analyzer. Further demonstration of porcelain compatibility was established by fabricating three-unit porcelain veneered fixed bridges using standard dental laboratory procedures and commercially available dental porcelain.[1] The completed bridges were free from defect in structure or appearance. The bond obtained between the alloy and the dental opaque porcelain was established to be excellent by water quenching the completed bridge from 950° C. The resulting fractures were predominantly outside the alloy-porcelain interface and in the porcelain.

[1] Cobond Ceramic Bonding Alloy-Instructions for Casting and Soldering (7/82), Dentsply International, York, PA 17405; and the Dentsply Biobond ® technique,-recommended technique for superior Porcelain-to-metal restorations, Dentsply International, York, PA (5/82).

EXAMPLE 7

Etch Bonding

The etch bond shear strength of the alloys of Examples 1 and 2 were compared to that of a commercially available nickel base alloy, Biobond TM C&B by bonding approximately 1 cm² areas of pairs of samples cast as 10 mm × 25 mm × 1 mm thick pieces with commercially available bonding resins after etching and cleaning the bonding surfaces following the commercial procedure recommended for the Biobond TM C&B Alloy.[2] The bonded samples were conditioned in 37° C. water for one week and pulled in tension to produce shear failure of the bond area. Table 4 shows the alloys of this invention displayed superior etched bond strength.

[2] The Dentsply Technique for Biobond ® Acid Etched Resin Bonded Bridgework brochure (1982) of Dentsply International Inc., York, PA 17405.

TABLE 4

Etch Bond Shear Strength

| Alloy | No Samples | Shear Strength Average | Standard Deviation |
|---|---|---|---|
| Example 1 | 10 | 2,900 psi | ±245 psi |
| Example 2 | 10 | 3,110 psi | ±405 psi |
| Biobond TM C & B | 11 | 2,110 psi | ±245 psi |

The alloys of Example 1 and 3 were cast to typical single unit crowns of a design usually veneered with resin base veneering materials. The resin veneer is retained on the casting by the mechanical interlocking of the resin around beads cast as a part of the casting surface. Unit of both alloys were veneered using the conventional bead retention or by etching and applying unfilled resin bonding agent prior to completion with the veneering resins. Completed crowns were conditioned for seven days in 37° C. water, and then cycled between 100° C. and 0° C. Under examination at a magnification of 10 times, the crowns fabricated with retention beads exhibited separation at the veneer-metal interfaces after ten thermal cycles, whereas no separation was observable with the etch bonded veneers on either alloy.

The alloys of this invention have microstructures that are favorable for selective etching to allow intimate mechanical bonding of veneering or denture base resin materials to the cast alloy substructure.

EXAMPLE 8

Castability

The alloys of Examples 1–3, were compared for castability to a commercially available nickel, chromium, and beryllium base alloy, Ticonium Premium 100, a product of the Ticonium Corporation, that is recommended for casting into gypsum investment to produce removable partial denture frameworks. The alloys were cast to castability test patterns described in Whitlock et al, *A Practical Test to Evaluate the Castability of Dental Alloys*, Paper #374, J. of Dental Research, 60, A, March '81, p. 404 with two patterns per casting ring. The patterns were oriented in the plane parallel to the axis of rotation of the centrifugal casting machine with one pattern behind the other such that the lagging pattern was in each case cast with higher force than the leading pattern. All castings were made in commercially available gypsum bonded investment at a mold burnout temperature of about 675° C. The results shown as percent completely cast pattern in Table 5 show the distinct improvement in castability of alloys of this invention over those of the prior art.

TABLE 5

| | Castability Percent Pattern Completely Cast | | | |
|---|---|---|---|---|
| | Alloy of Example 1 | Alloy of Example 2 | Alloy of Example 3 | Ticonium Premium 100 |
| Cast with high force | 100% | 99% | 100% | 81% |
| Cast with low force | 98% | 98% | 98% | 66% |

The invention has been described with reference to certain preferred embodiments thereof; however, the contemplated breadth of the composition and its application should be interpreted in light of the specification and claims to include further embodiments which employ equivalent materials for their stated function in the melt and finished alloy.

What is claimed is:

1. A nickel base casting alloy consisting essentially of by weight percent about:

Ni: 52–84
Cr: 10–25
(Cb)Nb: 3–10
Mn: 3–8
Be: 0.5–2.0.

2. The alloy of claim 1 wherein said alloy exhibits a solidus temperature below about 1,090° C. and tensile strength, ductility, and corrosion resistance properties suitable for use in the fabrication of cast dental prosthetic devices and cast jewelry.

3. The alloy of claim 1 further containing aluminum in an amount up to about 3 percent by weight.

4. The alloy of claim 1 further containing by weight percent up to about: 3.5 percent aluminum; 20 percent cobalt; 6 percent copper; 3 percent tin; 1 percent titanium; 5 percent vanadium; 8 percent each or in combination of molybdenum, tantalum and tungsten; 1 percent each or in combination of boron and carbon; 3 percent rare earth elements; and incidental impurities; said alloy consisting of at least about 71 percent by weight of nickel, chromium, niobium, manganese, and beryllium in combination.

5. A nickel base casting alloy consisting essentially of by weight percent about:

Ni: 65–84
Cr: 11–16
(Cb)Nb: 3.5–5.5
Mn: 3.5–4.5
Be: 0.85–1.15
Al: 0.8–2.5 wherein said alloy exhibits a solidus temperature between about 1,050° C. to about 1,070° C. and tensile strength, ductility, and corrosion resistance properties suitable for use in the fabrication of gypsum bonded investment cast dental prosthetic devices and jewelry.

6. A nickel-chromium-niobium-manganese-beryllium alloy having a solidus temperature below about 1,090° C., an ultimate tensile strength in excess of about 80,000 psi, a 0.2 percent offset tensile yield strength in excess of about 50,000 psi, and a coefficient of thermal expansion in the range of from about $13.0 \times 10^{-6}$ in/in/°C. to about $15.0 \times 10^{-6}$ in/in/°C., and consisting essentially of (by weight percent): from about 52 to 84 percent nickel, from about 10 to 25 percent chromium, from about 3 to 10 percent niobium, from about 3 to 8 percent manganese, and from about 0.5 to 2.0 percent beryllium.

7. The alloy of claim 6, further consisting essentially of aluminum in an amount up to about 3 percent by weight.

8. The alloy of claim 7 wherein aluminum is present in an amount between about 0.8 and about 2.5 percent by weight.

9. The alloy of claim 7 consisting essentially of (by weight percent) about:
Ni: 65–84
Cr: 11–16
(Cb)Nb: 3.5–5.5
Mn: 3.5–4.5
Be: 0.85–1.15
Al: 0.8–2.5

10. The alloy of claim 9 further containing by weight percent up to about: 20 percent cobalt, 6 percent copper; 3 percent tin; 1 percent titanium; 5 percent vanadium; 8 percent each or in combination of molybdenum, tantalum, and tungsten; 1 percent each or in combination of boron and carbon; 3 percent rare earth elements; and incidental impurities; said alloy consisting of at least about 83.85 percent by weight of nickel, chromium, niobium, manganese, and beryllium in combination.

11. An alloy suitable for use in the gypsum bonded investment casting of dental prosthetics and jewelry consisting essentially of (by weight percent): from about 52 to 84 percent nickel, from about 10 to 25 percent chromium, from about 3 to 10 percent niobium, from about 3 to 8 percent manganese, and from about 0.5 to 2.0 percent beryllium, said alloy exhibiting a solidus temperature between about 1,050° C. and about 1,070° C.

12. Dental work containing dental porcelain fused to a metal casting, said casting consisting of (by weight percent): an alloy consisting essentially of about 65 to 80 percent nickel, about 10 to 25 percent chromium, about 0.5 to 2.0 percent beryllium, about 3 to 8 percent manganese, and about 3 to 10 percent niobium.

13. The dental work of claim 12 wherein said alloy contains additionally aluminum in an amount up to about 3 percent by weight.

14. The dental work of claim 13 wherein said aluminum is present in an amount of from about 0.8 to 2.5 percent by weight.

* * * * *